United States Patent

Lankinen

Patent Number: 5,476,093
Date of Patent: Dec. 19, 1995

[54] DEVICE FOR MORE EFFECTIVE PULVERIZATION OF A POWDERED INHALATION MEDICAMENT

[75] Inventor: Tapio Lankinen, Turku, Finland

[73] Assignee: Huhtamaki Oy, Turku, Finland

[21] Appl. No.: 91,407

[22] Filed: Jul. 14, 1993

Related U.S. Application Data

[63] Continuation of Ser. No. 778,935, Feb. 14, 1992, abandoned.

[51] Int. Cl.$^6$ .......................... A61M 15/00; A61M 16/10
[52] U.S. Cl. .................... 128/203.15; 128/203.12
[58] Field of Search ................. 128/200.11, 200.14, 128/200.18, 200.21, 200.23, 200.24, 203.12, 203.15, 203.16, 203.21, 203.23, 204.14, 911, 912; 239/338, 370; 261/DIG. 65, DIG. 83; 241/5, 38, 9

[56] References Cited

U.S. PATENT DOCUMENTS

| | | | |
|---|---|---|---|
| 1,756,254 | 4/1930 | Lykken | 241/5 |
| 2,515,542 | 7/1950 | Yellott | 241/5 X |
| 2,517,482 | 8/1950 | Hall | 128/203.15 |
| 3,271,162 | 9/1966 | Bishop | 241/9 |
| 3,362,405 | 1/1968 | Hazel | 128/203.15 |
| 3,565,348 | 2/1971 | Dickerson et al. | 241/5 |
| 3,568,887 | 3/1971 | Jacobs | 222/129.4 X |
| 3,625,403 | 12/1971 | Rousselot . | |
| 3,726,484 | 4/1973 | Schurr | 241/5 |
| 3,795,244 | 3/1974 | Lax | 128/203.15 |
| 3,809,084 | 5/1974 | Hansen | 128/203.15 |
| 3,870,046 | 3/1975 | Elliott | 128/203.15 |
| 3,915,165 | 10/1975 | Rambosek | 128/203.15 |
| 3,918,451 | 11/1975 | Steil | 128/203.21 |

(List continued on next page.)

FOREIGN PATENT DOCUMENTS

| | | | |
|---|---|---|---|
| 56690 | 12/1990 | Chile . | |
| 5585 | 4/1979 | European Pat. Off. . | |
| 215559 | 7/1986 | European Pat. Off. . | |
| 791401 | 5/1985 | Finland . | |
| 71488 | 10/1986 | Finland . | |
| 871000 | 3/1987 | Finland . | |
| 552542 | 5/1923 | France | 128/200.18 |
| 777286 | 2/1935 | France | 128/200.21 |
| 1445520 | 6/1966 | France . | |
| 2449179 | 7/1980 | Germany . | |
| 3216022 | 11/1982 | Germany | 241/5 |
| 3612473 | 10/1987 | Germany | 128/203.15 |
| 556532 | 2/1957 | Italy | 128/200.18 |
| 990303 | 2/1983 | U.S.S.R. | 241/5 |
| 1282894 | 1/1987 | U.S.S.R. | 241/5 |
| 1503827 | 8/1989 | U.S.S.R. | 261/DIG. 26 |
| 12853 | 5/1912 | United Kingdom | 128/203.15 |
| 240358 | 10/1925 | United Kingdom | 128/200.14 |
| 1331216 | 9/1973 | United Kingdom . | |
| 1396258 | 6/1975 | United Kingdom . | |
| 2064334 | 6/1981 | United Kingdom | 128/203.15 |
| 8301915 | 6/1983 | WIPO | 241/5 |
| 8802267 | 4/1988 | WIPO | 128/200.23 |
| 8803419 | 5/1988 | WIPO | 128/200.23 |
| 9119524 | 12/1991 | WIPO | 128/203.15 |

OTHER PUBLICATIONS

International Search Report for PCT/FI90/00159.
Chilean Patent Office Action for 566–90.

Primary Examiner—Kimberly L. Asher
Attorney, Agent, or Firm—Rothwell, Figg, Ernst & Kurz

[57] ABSTRACT

A device for a more effective pulverization of particles and/or agglomerates of a powdered inhalation medicament, comprises a chamber suitable for receiving medicament which is substantially closed at one end thereof. The chamber is provided with at least one air inlet port and a powdered medicament outlet port. The chamber is rotationally symmetrical in shape and preferably its cross-section perpendicular to the center axis thereof is substantially circular in shape. The chamber also is without substantial flow obstacles. The inlet and outlet ports are spaced from each other in the direction of the center axis of chamber, with the inlet port being designed to direct the air inflow into the vortex chamber substantially parallel to the tangent of the chamber.

12 Claims, 3 Drawing Sheets

U.S. PATENT DOCUMENTS

| | | | |
|---|---|---|---|
| 3,991,761 | 11/1976 | Cocozza | 128/203.15 |
| 4,206,758 | 6/1980 | Hallworth | 128/203.15 |
| 4,249,526 | 2/1981 | Dean et al. | 128/203.15 |
| 4,423,724 | 1/1984 | Young | 128/203.15 |
| 4,429,835 | 2/1984 | Brugger | 239/338 |
| 4,452,239 | 6/1984 | Malem | 128/200.17 |
| 4,706,663 | 11/1987 | Makiej | 128/200.23 |
| 4,762,148 | 8/1988 | Marui et al. | 137/808 |
| 4,884,565 | 12/1989 | Cocozza | 128/203.21 |
| 4,907,583 | 3/1990 | Wetterlin | 128/203.15 |
| 4,940,051 | 7/1990 | Lankinen | 128/203.15 |
| 5,035,364 | 7/1991 | Escallon | 241/5 |
| 5,165,391 | 11/1992 | Chiesi | 128/200.23 |
| 5,186,166 | 2/1993 | Riggs | 128/203.15 |

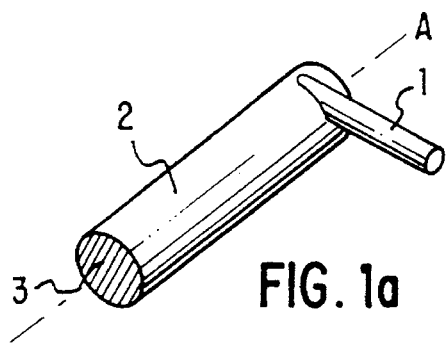 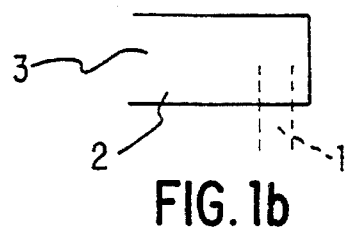
FIG. 1a  FIG. 1b
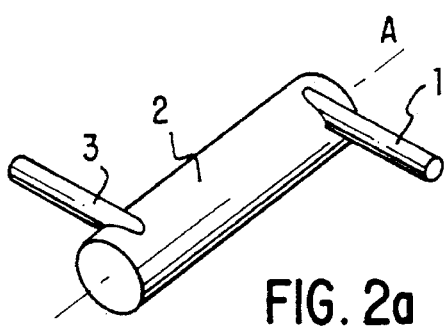 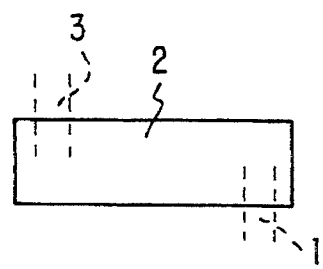
FIG. 2a  FIG. 2b
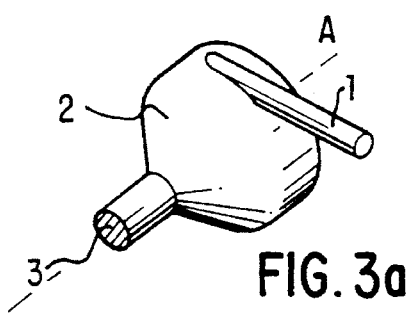 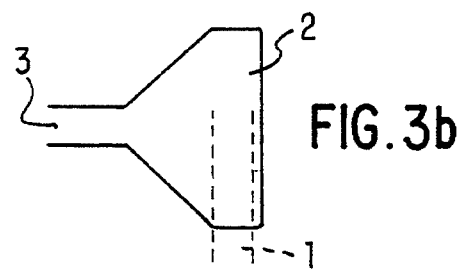
FIG. 3a  FIG. 3b
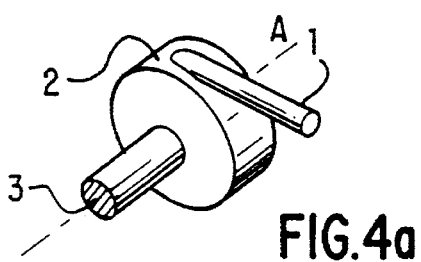 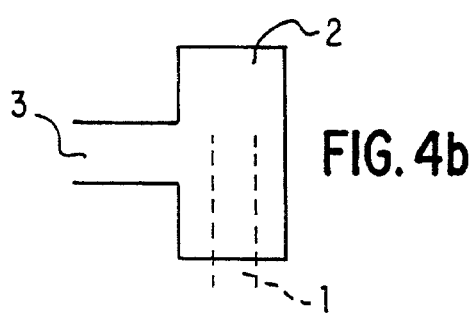
FIG. 4a  FIG. 4b
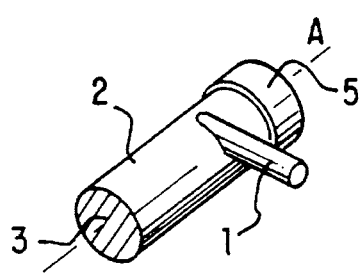 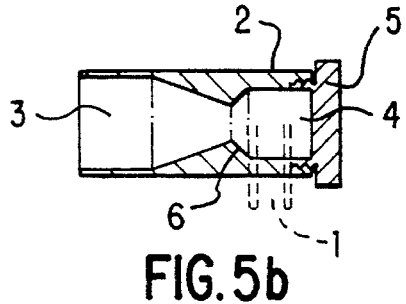
FIG. 5a  FIG. 5b

DEVICE FOR MORE EFFECTIVE PULVERIZATION OF A POWDERED INHALATION MEDICAMENT

This is a continuation of application Ser. No. 07/778,935, filed Feb. 14, 1992, now abandoned.

BACKGROUND OF THE INVENTION

1. Field of the Invention

The present invention relates to a device which is based on centrifugal force for achieving more effective pulverization of a powdered inhalation medicament in a manner that the penetration of medicament into the lungs is improved and the adhesion to the upper respiratory passages is reduced for alleviating the side effects caused thereby.

2. Description of the Related Art

It is generally known that the size of medicament particles should be 1–5 microns, preferably 2–3 microns, for the best possible penetration into their destination, i.e. deep into the lungs. The most common metering device is a so-called inhalation aerosol which is quite readily capable of reaching the optimal particle size. In addition to inhalation aerosols, an increasing number of powder inhalators are presently in use as these offer certain benefits, e.g. there is no need for ozone-destroying propellants. Several clinical studies have indicated that, with the same amount of medicament, the powder inhalators do not achieve the same effect as inhalation aerosols but it takes up to 2–3 times larger dosages to get the same results. The reason for this is considered to be the fact that a powdered medicament issuing from powder inhalators has too large a particle size. Thus, most of the medicine dosage coming out of inhalators is retained in upper respiratory passages which, with certain medicines, can cause serious side effects. The medicine dosages required for different inhalation medicaments vary considerably, the smallest being appr. 0.01 mg and the largest 20 mg. When small amounts of medicine are metered in powdered form, it is generally necessary to use some adjuvant or carrier, so that the sufficiently precise measuring of a dosage would be possible with the present technology. No matter if the dosage comprises just medicine or has a carrier admixed therein, the medicine dosage substantially comprises interadhered particles and most of these agglomerates are too large to penetrate into the lungs. As the agglomerates are released in a powder inhalator into an air flow passing into the lungs of a patient, there will occur some dispersal of these particle deposits, said dispersal resulting from the formulation of a powdered medicament and the construction of an inhalator. It is known that constructions creating a strong turbulence are capable of more effective pulverization.

In practice, however, no prior known powder inhalator structure and/or medicine formulation has produced results that would be equal to those achieved by an ordinary inhalation aerosol. It has been suggested as a partial solution that inhalation should be effected with as much force as possible, whereby the turbulence and pulverization of particles would accordingly be most effective. However, a quick inhalation is difficult for a person suffering e.g. from serious asthma and, on the other hand, a quick inhalation increases the residue in upper respiratory tracts. According to studies, pulverization of agglomerates is indeed intensified but the overall benefit is marginal. The best pulmonary penetration in relation to the adherence of medicament to upper respiratory tracts has been achieved by slow inhalation, corresponding to a flow rate of appr. 30 l/min or 0.5 l/sec.

The only prior known powder inhalator is the device described in Finnish Patent application No. 871000 which has been designed in an effort to produce a clearly defined turbulence for pulverizing agglomerations of medicine. The centrally directed deflectors inside the device or the helical chute are described as setting the air flow in a spinning motion, whereby the medicine particles entrapped in the air abrade as a result of centrifugal force against the walls of the structure as well as collide into each other with resulting pulverization. The device described in the cited application is a TURBUHALER® inhalator device marketed by Draco from Sweden. The pulverizing structure of the TURBUHALER® device is a helical chute or groove. Laboratory tests indicated that this device had a relatively good pulverization of agglomerates of medicine which could be greatly improved upon by means of a device of the present invention. In view of the pulverization of agglomerates or accumulations of medicine, there are a few defects in the device. The helical groove has in the centre thereof an open space having less air resistance than inside the groove. Accordingly, the flow rate of air and centrifugal force on the circumference of the groove are less than theoretical. Since the particles advance in the groove under a force caused by air resistance and centrifugal force tends to push the particles perpendicularly to the circumferential tangent, the actual force applied to the particles is a resultant of these forces and is applied diagonally relative to the circumferential tangent. Thus, the centrifugal force resulting from the spinning motion cannot be utilized to its full extent for the pulverization of accumulations. In all deflector structures according to the cited application, the particles escape from the device within a few thousandths of a second when using conventional inhalation rates of 30–60 l/min and that is a very short time for an effective pulverization. The residence time can be lengthened, e.g., by increasing the number of helices in groove portions or the number of separate deflector structures or the length of zigzagging air flow channels, but this would complicate manufacturing and cleaning and medicine residues in the actual device would increase. After all, cleaning of the structures disclosed in the cited application is difficult as it is.

The European Patent application No. 215559 discloses a powder inhalator, wherein one or more balls travel as a result of air flow around a periphery which is substantially circular in configuration. The air flow comes into contact with the periphery tangentially relative thereto. The medicine is adhered either to the surface of balls or to the surface of the circulation periphery from which it is removed and is pulverized by the action of the rolling balls. The device employs a centrifugal force for fractionating loose particles in a manner that the discharge of air occurs centrally relative to the circulating path. Thus, the pulverization of medicine is a result of a mechanical contact between the balls and the surface.

In the cited structure, the balls close the circulating path for the most part and, thus, there cannot be high speeds of circulation for the balls or medicine particles and, hence, there cannot be major centrifugal forces. It is obviously difficult to use the device for repeatedly metering out exact doses of medicine. The British Patent No. 1485163 describes a device, wherein a powdered medicament containing elongated capsule provided with pierced ends is set through the action of inhalation air in a rotating motion inside a cylindrical mixing chamber. Piercing of the capsule is effected in a capsule-shaped space which is in open communication with the mixing chamber and the capsule is jerked therefrom along with the air flow into the mixing chamber to spin around its vertical axis. The medicament flings through the ends of the capsule into the mixing chamber and further into an inhalation channel. The device according to this Patent is an INALATORE® I.S.F. inhalator device. Laboratory tests showed that the device had a reasonable pulverizing effect for accumulations of medicine but a distinctly poorer effect than what is achieved by a device of the present invention.

The device disclosed in the cited Patent would have an improved pulverizing effect if the rotating speed of a capsule and air in the mixing chamber could be increased by using the centrifugal force more effectively for pulverization. This is impossible with the cited structure since it is prevented by the own mass of a capsule and by the friction resulting from its rotation. In addition, the space in communication with the mixing chamber and intended for piercing the capsule is asymmetrical relative to the rotating direction and produces a decelerating turbulence.

British Patent No. 1331216 discloses a device operating on the capsule discharging mechanism, wherein the capsule, after piercing, is carried into a cylindrical mixing chamber by the action of inhalation. The air arrives in this chamber through a plurality of tubes directed tangentially to the circulation periphery setting the capsule in a rotating motion and transferring the medicine from the capsule into the inhalation air. This structure is also not capable of producing sufficient centrifugal forces for the pulverization of accumulations of medicine because of the capsule's mass, rotational friction and air resistance.

British Patent No. 1472650 discloses a device for the inhalation of a powdered medicament contained in a capsule. The capsule is purged in a manner that some of the inhalation air is passed through a pierced capsule while most of the air travels past the capsule. However, piercing of the capsule is effected centrally towards the longitudinal axis of the capsule and there is no purpose to create inside the capsule a turbulent flow that would produce a major centrifugal force. Also, according to laboratory tests, the device set forth in the cited Patent (Boehringer Ingelheim) did not produce a powerful turbulence inside the capsule. Also the pulverizing effect of the device for accumulations of medicine was conventional.

British Patent No. 1118341 describes a structure for purging an open, medicine-containing container into inhalation air. As one alternative to sucking the air into a chamber containing a medicine container there is shown a structure which uses deflectors for setting the air flow in a spinning motion in the chamber. The cited Patent specification discloses that an object is to create irregular turbulence and passage of air flows against the deflectors rather than to set the air in a rotating motion as rapid as possible. Thus, the internal positioning of deflectors in the chamber severely restricts the rotating motion but creates effectively other turbulence.

Prior known are also several structures, wherein a medicament-containing capsule is pierced prior to dosage, set in its holder in a rotating motion by means of inhalation air or cut open. Prior known are also structures, wherein a medicament is transferred from a capsule into inhalation air by the application of pressurized air. Furthermore, there are known structures, wherein a powdered medicament is transferred for inhalation from a disc or a separate powdered medicament container carrying several doses of medicine. See for example, U. S. Pat. Nos. 4,046,146; 4,116,195; 4,117,844; 4,210,140 and British Patents 1,182,779; 1,396,258; 1,404,338; 1,457,352; 1,459,426; 1,502,150; 1,521,000; or Finnish Patent publication 76258, Finnish applications 863094 and 883767, and Danish publication 153631B.

None of the above cited and examined publications discloses a structure, wherein a powdered medicament would be pulverized by means of inhalation or an external gas pressure by the application of a centrifugal force resulting primarily from a powerful rotating motion with a structure described hereinafter.

SUMMARY OF THE INVENTION

In a device of the invention, a powdered medicament intended for inhalation is pulverized on the basis of a sufficiently powerful centrifugal force prior to or during inhalation. The centrifugal force is produced through the action of inhalation or the flow of an external pressurized gas. In a device of the invention, a powdered medicament is entrapped in a gas flow and forced in a substantially circular or rotationally symmetrical space to such a powerful rotating motion that an effective splitting of accumulations of medicine is obtained. This is effected in a rotationally symmetrical chamber whose largest internal diameter can be 30 mm. With a device of the invention, the pulverization time of large, hard-splitting particles can be increased and, as the rotating motion is over, the major particles, e.g., the carrier, can be mostly retained in the chamber to prevent its passage into the repiratory tracts of a patient. A device of the invention is more effective than the prior known solutions, and thus, as well as by virtue of the ability of retaining large particles, it is possible to improve the effect of medication and to reduce the side effects caused by a medicament remaining in the upper respiratory tracts.

Upon the application of this device to inhalation conducted by a patient, it should be appreciated that the best penetration of medicine particles into the lungs is obtained by means of a slow inhalation with a duration of approximately 5 seconds. Thus, the inhalation rate will be 20–30 l/min. In order to facilitate such trouble-free operation, e.g., for a person with a difficult asthma, the inhalation resistance caused by the device itself may not be too high. However, all deviations from a laminar air flow add to the inhalation resistance in powder inhalators no matter how effectively such deviation or turbulence pulverizes accumulations of medicine. Because, however, the inhaling power of a patient sets a practical limit to the force that can be used in an inhalator for the pulverization of accumulations of medicine, the optimal exploitation of this force is of major importance in view of the proper operation of the device. When developing this device, various turbulences and collision patterns of particles were compared with centrifugal force and the latter was found overwhelmingly superior.

If a cylinder with one solid end is supplied with an air flow tangentially from the side at its solid end, such flow is first set in a rotating motion dictated by its entrance speed which produces a centrifugal force. Magnitude of this force can be calculated from the formula:

$$a = -\frac{v^2}{r}$$

wherein a=acceleration v=air flow rate r=radius of cylinder When gravity acts on a mass at an acceleration of 9.91 m/s$^2$, the a: 9.91 m/s$^2$ indicates the number of times the mass (weight) of a particle circulating along the inner wall of a cylinder entrapped in an air flow is multiplied as a result of the centrifugal force.

If in such a well-operating device (FIG. 1) the radius of an inlet tube is 3 mm and the radius of a vortex cylinder is 6 mm, the suction rate of 30 l/min corresponding to a slow inhalation provides a maximal air circulation rate of 17.68 m/s in the cylinder and an acceleration of $52.1 \times 10^3$ m/s$^2$, the latter being 5310 times the acceleration of gravity. According to this, the weight of medicine particles would be multiplied by more than 5000, which fully explains the power of the device. When measuring the negative pressure caused by inhalation at a suction rate of 0.5 l/s, the reading was −15 mbar but when inhalating in the reverse direction, the reading was just −4.5 mbar. The difference reflects the energy required for the generation of a centrifugal force since, when inhalating in the reverse direction, there will be no turbulent flow and air resistance is quite close to that of a laminar flow. Tests on patients have revealed, that the inhalation resistance should not exceed the reading corresponding to a negative pressure of 15–20 mbar. On the other hand, a suitable inhalation resistance can be used to prevent too fast an inhalation as the latter would increase the medicine residue in upper respiratory tracts. Hence, in a device of the invention it is possible to set a particular inhalation resistance by adjusting the diameter of an inlet tube and that of the cylinder while the force of inhalation can still be effectively used for the pulverization of accumulations of medicine. If the centrifugal force is produced by the application of a pressurized gas, e.g., compressed air, the physiology of a patient no longer controls the power of the device. Thus, the diameter of cylinder and inlet tube can be reduced. In a device in which the inlet tube had a diameter of 1 mm and the cylinder had a diameter of 4 mm, the 1.2 bar overpressurized air had a measured air flow rate through the device of 4.5 l/min. Thus, the air flow rate in the inlet tube and on the periphery of the cylinder was 95.5 m/s which, in accordance with the above-described formula, provides 465,000 times the gravitational acceleration when the speed of rotation is 7600 r/s. In this context, it should be appreciated that the circulating speed of particles is considerably slower than the calculated readings as a result of, e.g., air resistance and abrasive-friction, but the calculations provide an impression of the magnitude of those forces involved in the operation of the device. An instantaneous positive pressure of appr. 1 bar can even be reached with a manually operated pumpet and higher pressures can be obtained by using, e.g., a manually or electrically rechargeable pressure container.

Because of the operating principle of the device, the cylinder cannot be allowed to contain any structures substantially impeding free air circulation, such as deflectors, grooves or capsules or parts thereof spinning along with the air flow, with the exception of carriers containing medicine particles or a formulation. Even the relatively large amounts of carriers contained in certain medical formulations clearly hamper and decrease the speed of rotation. The cylinder must have a cross-section which is substantially circular in every part thereof. However, this makes it possible that the cylinder can have a cross-section which is conical or symmetrically formed for using centrifugal force to fractionate particles by the application of generally known centrifugation principles. A rotationally symmetrical axle or a part thereof extending in the same direction as the longitudinal, liner, axis A of a vortex chamber does not disturb the action.

FIG. 1a illustrates a cylindrical device according to this invention showing the form of an equiradius circle, FIG. 1b being a cross-section thereof.

FIG. 2a illustrates a cylinder according to this invention showing both ends are solid, and both the entrance and exit of air occur tangentially, FIG. 2b being a cross-section thereof.

FIG. 3a illustrates an embodiment according to this invention showing a conical shape, FIG. 3b being a cross-section thereof.

FIG. 4a illustrates an embodiment according to this invention showing a quadratic shape, the discharge being effected centrally through the gable of the cylinder, FIG. 4b being a cross-section thereof.

FIG. 5a illustrates an embodiment of this invention comprising a removable plug, FIG. 5b being a cross-section thereof.

Figure 6A:
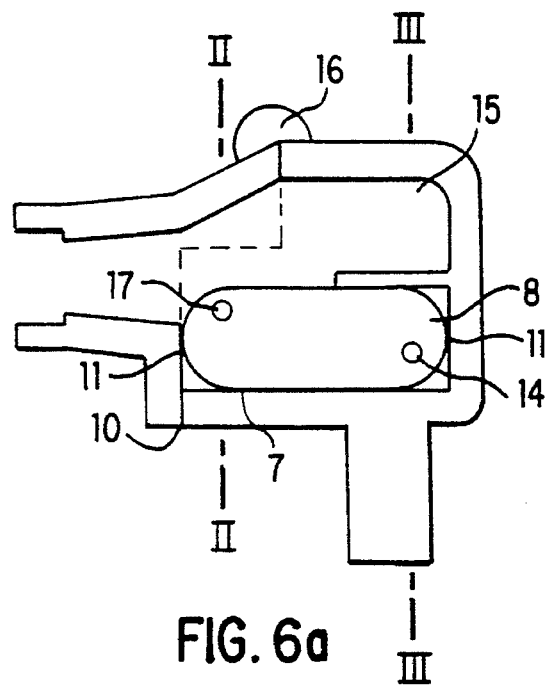
Figure 6B:
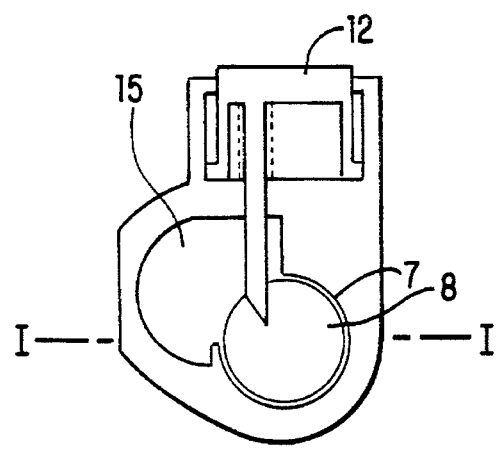
Figure 6C:
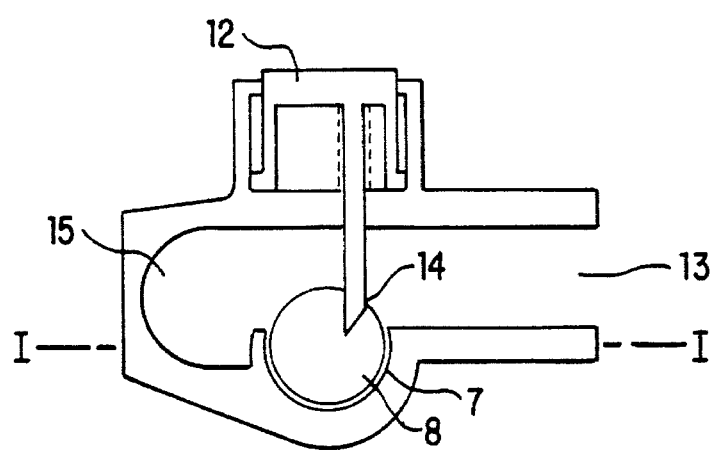

FIG. 6a–FIG. 6c illustrate an embodiment of this invention wherein conventional powder capsules are used as a vortex chamber. FIG. 6a shows an axial section of a capsule along plane A illustrated in FIG. 6b. FIG. 6b shows a section of a capsule along plane B illustrated in FIG. 6a wherein plane B is perpendicular to plane A. FIG. 6c shows a section of a capsule along plane C in FIG. 6a wherein plane C is perpendicular to plane A.

Figure 7:
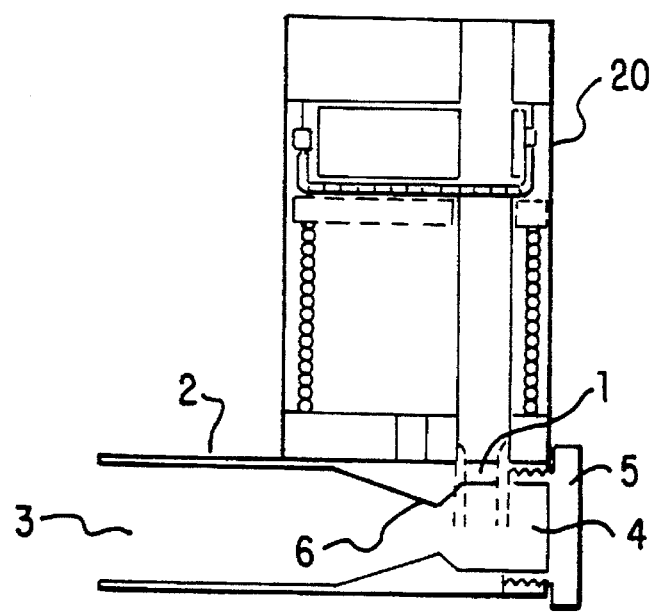

FIG. 7 illustrates a device as shown in FIG. 5 which is connected to a prior art powder inhalator.

Figure 8:
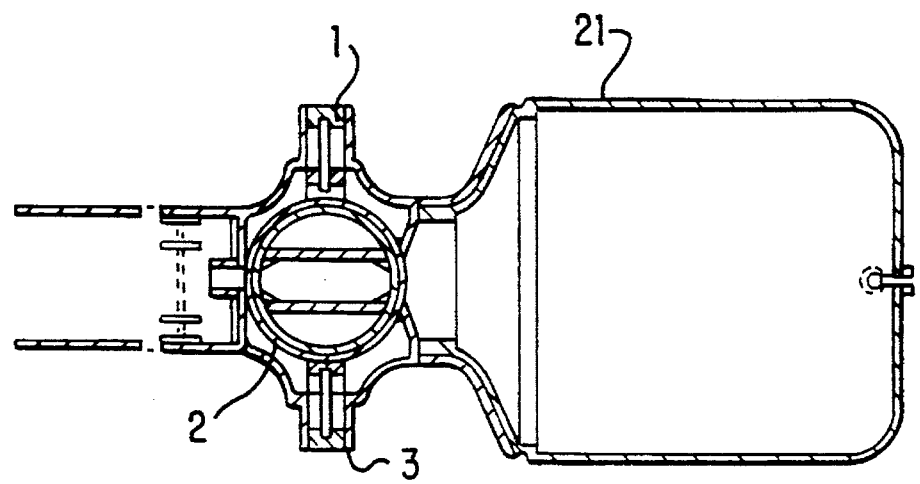

FIG. 8 illustrates a device as shown in FIG. 2 connected to another prior art powder inhalator.

In the structures illustrated in FIGS. 1–4, during a circulating motion, there occurs fractionation of particles in a manner that larger particles tend to circulate continuously on the largest periphery of the cylinder and shall not be able to escape through the central outlet port until pulverized to sufficient fineness.

DESCRIPTION OF THE PREFERRED EMBODIMENTS

It has been found through experimentation that the pulverization time of large particles is increased if the structure of FIG. 3a or 4a is alongside the inlet tube provided with a solid chamber extension, At the end of the air flow, the non-pulverized particles are mostly retained in this space and cannot work their way into the pharynx of a patient. FIG. 5a shows a more detailed structural drawing of such a vortex chamber. The medicine agglomerates arrive along with an air flow from a tube 1 into a chamber provided with a constriction 2 for preventing the immediate departure of large particles from the chamber under the action of a centrifugal force. The large particles are able to rotate and spin in a closed chamber section 3 and, after a sufficient pulverization, are able to escape into an inhalation tube 4. The closed chamber section comprises a removable plug 5 for facilitating the cleaning of the chamber. The optimum diameter of a vortex chamber operating by the action of inhalation is 10–20 mm. The pulverization effect is excellent and the substantially tangential setting of an inlet tube is possible as long as the air resistance remains reasonable. If the diameter is increased, the pulverization effect deteriorates in a manner that, with a diameter of more than 30 mm, the pulverization effect is no longer significant.

It should be noted that a conventional powdered medicament capsule can also be used as a vortex chamber with suitable provisions. FIG. 6a, FIG. 6b and FIG. 6c illustrate an example of such a device whose operation is based on an air flow produced by inhalation. FIG. 6*a* shows a section in the axial direction of a capsule on plane A and FIGS. 6*b* and 6*c* show sections perpendicularly to the preceding one on planes B and C. A medicine capsule 8 is placed in a cylindrical space 7. Therefore, the device is hinged at 16 and opens along a line 9. A latch (not shown in the figures) indicated at 10 locks the parts to each other so as to immobilize the capsule by tightening at 11. The capsule is pierced by means of a dowel device 12 at both ends thereof in a manner that the air inflow through a tube 13 is tangentially directed into a hole 14. Most of the air flows past hole 14 into a space 15 provided at a hole 17 with a constriction producing a Venturi effect. Thus, there is a positive pressure at hole 14 and a negative pressure at hole 17 which intensifies the creation of a turbulent flow inside the capsule. The device can be connected to vortex chambers as shown in FIGS. 1*a*–5*a* for obtaining a complete powder inhaler fitted with a dual vortex chamber.

When operating a device as shown in FIGS. 6*a*–6*c* by the action of inhalation, said holes 14 and 17 must be sufficiently large for producing a sufficient turbulence inside the capsule. This requires that the capsule be made of some tough material for preventing fractures when piercing the holes. Also the size and shape of a capsule are significant factors. A capsule with flat ends serves the purpose better than a traditional round-headed capsule.

With a more intense air flow the pulverization effect of a device as shown in FIGS. 6*a*–6*c* can be improved. This can be achieved, e.g., by using a hand pumpet to pass a small amount of pressurized air into hole 17. In that case, inhalation must be effected simultaneously by pressing a pumpet unless some structures are used for retaining the pulverized particles for subsequent inhalation.

The devices shown in FIGS. 1*a*–5*a* can be connected to all available powder inhalators. In FIG. 7, a device as shown in FIG. 5*a* is connected to a TURBUHALER® powder inhalator 20 described in Finnish Patent application No. 871000 in a manner that the device replaces the helical groove included in TURBUHALER® inhalator.

In FIG. 8, a version of the device shown in FIG. 2*a* fitted with two outlet tubes is connected to a powder inhalator 21 described in Finnish Patent application No. 883767, wherein a medicine capsule is emptied by means of compressed air produced with a hand pumpet. In this combination, inhalation must occur at the same time that the pumpet is pressed.

Inhalation air is picked up from the area alongside the vortex chamber outlet tubes.

The ability of this invention to operate is highly dependent on the properties of the medicament used and any additives used. In order to achieve the best possible result, different medical formulations require the use of different vortex chamber designs. The manufacturing material of a vortex chamber must also be selected in a manner such that there is as little adherence of medicament to the chamber as possible and that the chamber has an inner surface which withstands major abrasive forces without excessive wear.

The power of a device of the invention has been studied by the application of a method generally used in this field, wherein the inhalation effected by a patient is simulated to suck a powdered medicament into a particle separator (a cascade impactor). This is to find out the number and mean particle size of those medicine particles that are capable of passing into their pulmonary site of action (less than 5.8 microns).

The following table illustrates results of the outputs of a device of the invention as well as prior known powder inhalators included as a reference.

| Powdered medicine | Inhalator | % of particles less than 5.8 microns of a dosage | Mean particle size (micron) | Patent reference to inhalator |
|---|---|---|---|---|
| 1.1 Ventoline 0.2 mg Rotacaps | ROTOHALER ® | 22.7 | 7.6 | Danish publ. No. 153631 B |
| 1.2 Ventoline 0.2 mg Rotacaps | INALATORE ® I.S.F. | 30.3 | 5.8 | GB 1485163 |
| 1.3 Ventodisks 0.2 mg | DISKHALER ® | 26.0 | 5.8 | Finnish Pat. appl. No. 863094 |
| 1.4 Ventoline 0.2 mg Rotacaps | FIG. 5 Prototype | 61.6 | 2.4 | |
| 2.1 Lomudal 20 mg caps. | SPINNHALER ® | 14.0 | 9.0 | GB 1182779 |
| 2.2 Lomudal 20 mg caps. | FIG. 5 Prototype | 38.2 | 2.3 | |
| 3.1 Bricanyl 0,5 mg | TURBUHALER ® | 35.5 | 4.1 | Finnish Pat. appl. No. 871000 |
| 3.2 Bricanyl 0,5 mg | FIG. 4 Prototype | 58.3 | 2.4 | |

In order to obtain comparable results, all reference groups employed the same pharmaceutical formulations:

1.1–1.4 salbutamol as pharmaceutical, lactose as carrier (Glaxo, GB)

2.1–2.2 Na-chromokligate as pharmaceutical, no carrier (Fisons, GB)

3.1–3.2 terbutaline as pharmaceutical, no carrier (Draco, S)

In embodiments of the invention, the dosage of a powdered medicine was effected by means of the metering unit of a powder inhalator disclosed in U.S. Pat. No. 4,046,146 which, if used by itself, does not produce distinct particles as obtained by a manual powder feeding device. Other inhalators included in the comparison are commercially available. The results take into consideration the medicament in the metering unit and inhalators.

When assessing the results, an objective of powder inhalators should also be considered: to administer to the patient as much a medicine dose having particles whose size is 1–5 microns, preferably 2–3 microns, for the most likely pulmonary penetration.

In all reference groups, the device of this invention was superior. The number of pharmaceutical particles of the proper size category was 1.6–2.7 times more than that of reference particles and the particles had exactly the optimum mean size.

Thus, a device of the invention is capable of improving the penetration of medicine into the lungs and, thus, reducing the residue in upper respiratory tracts for alleviating the side effects caused thereby. The present structures are readily cleanable, for example, with a small brush. The structures can be readily manufactured, for example, by pressure casting plastics. A device of the invention can be connected to prior known powder inhalators. It can be used both with separate medicine capsules and in association with a powder container containing a plurality of doses. The device operates both through the action of inhalation and pressurized gas, e.g., air.

I claim:

1. A device for pulverization of particle agglomerates into a single dose of powdered inhalation medicament for a powder inhalator, wherein the device comprises a vortex chamber suitable for receiving powdered medicament, a chamber end which is substantially closed and which does not comprise any receptacle containing powdered medicament, at least one air inlet through which the agglomerates are introduced into said chamber without pressurized propellant gas, and an outlet for directing air and medicament into the oral and/or nasal cavities of the user of the device, further wherein the vortex chamber is rotationally symmetrical in an arcuate shape around a longitudinal, linear center axis of rotation of air flow within the vortex chamber and is free of obstacles which substantially affect air circulation within said vortex chamber, said inlet and outlet being spaced from each other in a direction along the longitudinal, linear center axis of the vortex chamber, and said inlet being configured to direct air inflow into and along the inlet in a direction that is substantially tangential to the vortex chamber and not toward said center axis.

2. A device according to claim 1 wherein said inlet is located in a wall of said vortex chamber adjacent to the substantially closed end of the vortex chamber.

3. A device according to claim 1 wherein the vortex chamber comprises two ends and both ends are substantially closed.

4. A device according to claim 1 wherein the vortex chamber has a diameter which varies in a stepless fashion.

5. A device according to claim 2 wherein the vortex chamber has a diameter which varies in a stepwise fashion.

6. A device according to claim 1, 2 or 3 further comprising a constriction for retaining major particles, wherein said constriction is located between said vortex chamber and said outlet.

7. A device according to claim 1 or 2 wherein the closed end of said vortex chamber comprises a removable plug.

8. A device according to claim 1 wherein said vortex chamber has a cross-section perpendicular to the center axis thereof which is substantially circular in shape.

9. A powder inahalator device for the inhalation of powdered medicament comprising a device which comprises a vortex chamber suitable for receiving powdered medicament, a chamber end which is substantially closed and which does not comprise any receptacle containing powdered medicament, at least one air inlet through which powdered medicament is introduced into said chamber without pressurized propellant gas, and an outlet for directing air and powdered medicament into the oral and/or nasal cavities of the user of the device, further wherein the vortex chamber is rotationally symmetrical in an arcuate shape around a longitudinal, linear center axis of rotation of air flow within the vortex chamber and is free of obstacles which substantially affect air circulation within said vortex chamber, said inlet and outlet being spaced from each other in a direction along the longitudinal, linear center axis of the vortex chamber, and said inlet being configured to direct air inflow into and along the inlet in a direction that is substantially tangential no the vortex chamber and not toward said center axis.

10. An inhalator device according to claim 9 wherein said inlet is located in a wall of said vortex chamber adjacent to the closed end of the vortex chamber.

11. An inhalator device according to claim 9 wherein the vortex chamber comprises two ends and both ends are substantially closed.

12. A device for pulverization of particle agglomerates of powdered inhalation medicament for a powder inhalator, wherein the device comprises a vortex chamber receiving only a single dose of powdered inhalation medicament without pressurized propellant gas, a chamber end which is substantially closed, at least one air inlet adjacent said closed end, and an outlet for directing air and medicament into the oral and/or nasal cavities of the user of the device, further wherein the vortex chamber is rotationally symmetrical in an arcuate shape around a longitudinal, linear center axis of rotation of air flow within the vortex chamber and is free of obstacles which substantially affect air circulation within said vortex chamber, said inlet and outlet being spaced from each other in a direction along the longitudinal, linear center axis of the vortex chamber, and said inlet being configured to direct air inflow into and along the inlet in a direction that is substantially tangential to the vortex chamber and not toward said center axis.

* * * * *